United States Patent
Morfill et al.

(10) Patent No.: US 9,889,218 B2
(45) Date of Patent: Feb. 13, 2018

(54) ELECTRODE ARRANGEMENT FOR GENERATING A NON-THERMAL PLASMA

(75) Inventors: Gregor Eugen Morfill, München (DE); Bernd Steffes, Garching (DE); Tetsuji Shimizu, Garching (DE)

(73) Assignee: MAX-PLANCK-GESELLSCHAFT ZUR FOERDERUNG DER WISSENSCHAFTEN E.V., Munich (DE)

( * ) Notice: Subject to any disclaimer, the term of this patent is extended or adjusted under 35 U.S.C. 154(b) by 1340 days.

(21) Appl. No.: 13/201,849

(22) PCT Filed: Mar. 13, 2009

(86) PCT No.: PCT/EP2009/001851
§ 371 (c)(1),
(2), (4) Date: Nov. 1, 2011

(87) PCT Pub. No.: WO2010/094304
PCT Pub. Date: Aug. 26, 2010

(65) Prior Publication Data
US 2012/0046597 A1 Feb. 23, 2012

(30) Foreign Application Priority Data
Feb. 17, 2009 (EP) .................................... 09002200

(51) Int. Cl.
*A61L 2/14* (2006.01)
*H05H 1/24* (2006.01)

(52) U.S. Cl.
CPC .............. *A61L 2/14* (2013.01); *H05H 1/2406* (2013.01); *H05H 2001/2431* (2013.01); *H05H 2001/2443* (2013.01)

(58) Field of Classification Search
CPC ... A61K 33/00; A61F 13/00; A61F 13/00051; A61L 2/14; H05H 1/2406;
(Continued)

(56) References Cited

U.S. PATENT DOCUMENTS 5,895,558 A * 4/1999 Spence ................... 204/164
6,629,974 B2 * 10/2003 Penny ................ A61B 18/042
128/898
(Continued)

FOREIGN PATENT DOCUMENTS

EP 1161267 B1 3/2000
EP 1 765 044 A 3/2007
(Continued)

OTHER PUBLICATIONS

International Search Report and Written Opinion and International Preliminary Report on Patentability for PCT/EP2009/001851, dated Dec. 4, 2009.

(Continued)

*Primary Examiner* — Kari Rodriquez
*Assistant Examiner* — Raymond E Harris
(74) *Attorney, Agent, or Firm* — Kilpatrick Townsend & Stockton LLP

(57) ABSTRACT

The invention relates to an electrode arrangement (1) for generating a non-thermal plasma, comprising: a layer-shaped first electrode (2) made of an electrically conductive material, a layer-shaped second electrode (4) made of an electrically conductive material, wherein the second electrode (4) is electrically insulated from the first electrode (2), and a dielectric barrier (3) being arranged between the first electrode (2) and the second electrode (4), so that the non-thermal plasma is generated by a dielectric barrier discharge. The inventive electrode arrangement is characterized in that at least one of the first electrode (2) and the second electrode (4) comprises several perforations which are distributed over the electrode.

31 Claims, 7 Drawing Sheets

(58) Field of Classification Search
CPC ... H05H 2001/2431; H05H 2001/2443; H05H 2001/245
USPC ...... 422/186.24, 22; 426/237, 247; 204/164; 602/2, 41–43; 604/23
See application file for complete search history.

(56) References Cited

U.S. PATENT DOCUMENTS

| | | |
|---|---|---|
| 6,911,225 B2 | 6/2005 | Ruan et al. |
| 8,852,389 B2 * | 10/2014 | Monden ............ H01J 37/32192 118/723 ME |
| 8,857,371 B2 * | 10/2014 | Tabata ................ C23C 16/505 118/723 E |
| 2001/0034519 A1 * | 10/2001 | Goble .................. A61B 18/042 606/41 |
| 2005/0118350 A1 * | 6/2005 | Koulik .................... H05H 1/44 427/535 |
| 2007/0253865 A1 | 11/2007 | Tsutsui et al. |
| 2008/0125775 A1 | 5/2008 | Morris |
| 2008/0138534 A1 | 6/2008 | Dineff et al. |
| 2008/0193329 A1 * | 8/2008 | Akishev ................ H05H 1/24 422/22 |
| 2010/0145253 A1 * | 6/2010 | Gutsol ................ A61B 18/042 604/20 |

FOREIGN PATENT DOCUMENTS

| | | |
|---|---|---|
| EP | 1925190 A | 5/2008 |
| JP | 2002-538896 T2 | 11/2002 |
| JP | 2003-123940 A | 4/2003 |
| JP | 2003-525655 T2 | 9/2003 |
| JP | 2005-504560 T2 | 2/2005 |
| JP | 2006-503609 T2 | 2/2006 |
| JP | 2006-075358 A2 | 3/2006 |
| JP | 2006-198029 A | 8/2006 |
| JP | 2008-130343 A | 6/2008 |
| WO | WO 95/09256 A1 | 4/1995 |
| WO | WO 99/12638 A1 | 3/1999 |
| WO | 00/54819 A1 | 9/2000 |
| WO | WO 00/67805 A1 | 11/2000 |
| WO | 02/067797 A2 | 9/2002 |
| WO | 02/099836 A1 | 12/2002 |
| WO | 2004/014439 A2 | 2/2004 |
| WO | 2007/031250 A1 | 3/2007 |
| WO | 2008/138504 A1 | 11/2008 |

OTHER PUBLICATIONS

Japanese Office Action issued in Japanese Application No. 2011-550419 dated Nov. 5, 2013 (9 pages).
Extended European Search Report dated Jul. 14, 2009, from European Application No. 09002200.5 (7 pages).

* cited by examiner

ELECTRODE ARRANGEMENT FOR GENERATING A NON-THERMAL PLASMA

CROSS-REFERENCE TO RELATED APPLICATIONS

This application is the U.S. National Stage entry of International Application No. PCT/EP2009/001851, filed Mar. 13, 2009, which claims benefit of European Application No. 09002200.5, filed Feb. 17, 2009. The contents of each are herein incorporated by reference in their entireties.

FIELD OF THE INVENTION

The invention relates to an electrode arrangement for generating a non-thermal plasma, particularly for the treatment of patients.

BACKGROUND OF THE INVENTION

The use of non-thermal plasma for the treatment of wounds and especially for the in-vivo sterilization, decontamination or disinfection of wounds is disclosed, for example, in WO 2007/031250 A1 and PCT/EP2008/003568.

However, these conventional devices for plasma treatment comprise complex electrode arrangements which are expensive and difficult to manufacture.

SUMMARY OF THE INVENTION

Therefore, it is a general object of the invention to provide an improved electrode arrangement for the generation of a non-thermal plasma.

This object is achieved by a novel electrode arrangement according to the main claim.

The electrode arrangement according to the invention comprises layer-shaped first and second electrodes made of an electrically conductive material, wherein the first and second electrodes are electrically insulated from each other by a dielectric barrier which is arranged between the first electrode and the second electrode, so that the non-thermal plasma is generated by a dielectric barrier discharge (DBD) which is well known in the state of the art and therefore needs no further explanation. The novel electrode arrangement according to the invention is characterized in that at least one of the first electrode and the second electrode comprises several perforations which are distributed over the electrode. Therefore, the plasma is produced within the perforations of the electrode.

In a preferred embodiment of the invention, at least one of the first electrode and the second electrode comprises a wire-mesh, wherein the afore-mentioned perforations are arranged between individual meshes of the wire-mesh. In other words, each mesh of the wire-mesh forms one of the afore-mentioned perforations. One advantage of such an arrangement is that it is scalable, adaptive and can be customized to any form and shape thereby allowing new applications, e.g. as a wound dressing which will be described in more detail later. Further, such an electrode arrangement is easy to manufacture and very cost-effective. Unlike conventional dielectric barrier devices proposed for plasma medicine, it does not pass a current through human tissue. Moreover, a double mesh system can be gas permeable so that a gas flow can transversely penetrate the electrode arrangement so that it is useful for air purification, sterilization and pollution (exhaust) control.

Further, it is possible to arrange several of the afore-mentioned double-mesh electrode systems at distances of a few centimeters, wherein the double-mesh systems are preferably aligned parallel to each other.

In another embodiment of the invention, at least one of the first electrode and the second electrode comprises a perforated plate in which the afore-mentioned perforations are arranged. For example, the plate can be made of copper or aluminium wherein the perforations in the plate are punched out of the plate. Further, it is possible that both electrodes of the electrode arrangement consist of perforated plates which are separated by the dielectric barrier.

In yet another embodiment of the invention, at least one of the first and second electrodes consists of parallel wires or stripes made of an electrically conductive material.

It should further be noted that in the afore-mentioned embodiments of the invention, the perforations are preferably equally distributed over the electrode surface so that the intensity of the plasma generation is also equally distributed over the surface of the electrode.

In one embodiment of the invention, the first electrode comprises a plate made of an electrically conductive material, wherein the plate is preferably massive and does not comprise any perforations. The dielectric barrier is substantially layer-shaped and formed on a surface of the plate. For example, the dielectric barrier can have a thickness in the range of 0.5-1 mm. In this embodiment, the second electrode comprises either the afore-mentioned wire-mesh or a perforated plate made of an electrically conductive material. The first electrode formed as a massive plate is preferably energized with an alternating current with a voltage of 10-20 kV and a typical electrical current of 10-30 mA while the second electrode formed as a wire-mesh is preferably electrically grounded.

In another embodiment of the invention, both the first electrode and the second electrode comprise a wire-mesh while the dielectric barrier comprises a cladding made of an electrically insulating and dielectric material surrounding the wires of at least one of the first electrode and the second electrode thereby electrically insulating the first electrode from the second electrode. In other words, the electrically insulating and dielectric cladding of the individual wires of the wire-mesh forms the dielectric barrier. The first electrode and the second electrode are attached to each other, preferably by an adhesive bond, so that the wire-meshs of the first and second electrodes are contacting each other physically.

In one variant of this embodiment, both the first electrode and the second electrode comprises a cladding surrounding the individual wires of the wire-mesh thereby forming the dielectric barrier.

In another variant of this embodiment, merely one of the first and second electrodes comprises a cladding surrounding the individual wires of the wire-mesh thereby forming the dielectric barrier. In other words, only one of the first and second electrodes is electrically insulated by a cladding while the other one of the first and second electrodes is not insulated by a cladding.

It should further be noted that the invention is not restricted to embodiments comprising just two electrodes. For example, it is possible to provide a third electrode and a further dielectric barrier so that there are two dielectric barrier discharge arrangements on both sides of a centre electrode thereby forming a sandwich-like arrangement.

It has already been mentioned that the electrodes are preferably adhered to each other. It is also possible that the dielectric barrier is adhered to at least one of the first and second electrodes.

In a further embodiment of the invention, the electrode arrangement is shaped in the form of a hollow tube having an axially aligned inlet for introducing a carrier gas into the tube and an axially aligned outlet for dispensing the non-thermal plasma out of the tube, so that the plasma is generated within the tube.

In one variant of this tube-shaped arrangement, the wall of the tube consists of a DBD arrangement comprising the afore-mentioned first and second electrodes and the dielectric barrier.

In another variant of this embodiment, the first electrode and the second electrode are arranged within the tube, wherein the first electrode and the second electrode are preferably linear electrodes, which are aligned substantially coaxially within the tube. At least one of the first electrode and the second electrode is preferably surrounded by a cladding made of an electrically insulating and dielectric material forming the dielectric barrier.

In other words, the electrodes of the DBD arrangement can either be arranged within the tube-shaped electrode arrangement or in the wall of the tube-shaped electrode arrangement.

It should further be noted that the entire electrode arrangement can be flat, two-dimensional, planar and/or curved. In other words, the novel electrode arrangement according to the invention can easily be adapted to any desirable shape.

Preferably, the electrode arrangement is substantially two-dimensional, flat and deformable so that the shape of the entire electrode arrangement can be adapted to the contour of a body part which is to be treated. Such an arrangement allows the use of the inventive electrode arrangement in a wound dressing which will be described in more detail later.

In another embodiment of the invention, the electrode arrangement further comprises a cover which is covering the electrode arrangement. The cover can be adapted to increase the local density of the reactive species of the plasma thereby reducing the time needed for a sterilization. Further, the cover can be adapted to filter out unused reactive species. It is further possible to adapt the cover to effect a better control of the plasma. Finally, the cover can be adapted so that the electrode arrangement can operate under reduced pressure.

The dielectric barrier consists of an electrically insulating and dielectric material. The dielectric barrier preferably consists of ceramics if high performance is desired. Alternatively, the dielectric barrier can be made of polytetrafluoroethylene if a lower performance of the electrode arrangement is sufficient. Further, the dielectric barrier can be made of polyethylene terephtalate (PET), flexible or rigid glass-ceramic, glas, Mylar®, casting ceramic or oxides. However, the melting point of the dielectric material should preferably be over +100° C.

It should further be noted that the invention is not restricted to an electrode arrangement as a single component. The invention rather comprises a complete apparatus for plasma treatment comprising the afore-mentioned novel electrode arrangement for generating the non-thermal plasma.

In one embodiment of the invention, such an apparatus is adapted to sterilize a hand of a human being by applying the non-thermal plasma to the hand. Such an apparatus comprises a housing for temporarily receiving the hand during sterilization and for applying the plasma to the hand within the housing. Further, the housing comprises an inlet opening for introducing the hand through the inlet opening into the housing. The afore-mentioned embodiment for sterilization of a hand is disclosed in detail in EP 09002200.5 which is therefore incorporated herein by reference.

In another embodiment of the inventive apparatus, the electrode arrangement is shaped in the form of a hollow tube having an axially aligned inlet for introducing a carrier gas into the tube and an axially aligned outlet for dispensing the non-thermal plasma out of the tube, so that the plasma is generated within the tube. The apparatus preferably comprises a fan or a compressor for blowing the carrier gas into the inlet of the tube-shaped electrode arrangement and axially through the tube-shaped electrode arrangement. Further, a nozzle can be attached to the outlet of the tube-shaped electrode arrangement for forming the plasma jet leaving the apparatus.

It is further possible to attach a guide pipe to the outlet of the electrode arrangement wherein the guide pipe directs the plasma jet in a specific direction. The afore-mentioned guide pipe is preferably flexible so that the direction of the plasma jet can be changed by aiming the guide pipe at a desired location of treatment.

In another embodiment of the invention, the apparatus is adapted to clean air from pollutants, particularly bacteria, viruses or spores.

In one variant of this embodiment, the electrode arrangement is permeable to gas and the polluted air transversely passes through the electrode arrangement so that the electrode arrangement cleans the air from the pollutants while the polluted air passes through the electrode arrangement.

In another variant of this embodiment, the electrode arrangement is tube-shaped and the polluted air axially passes through the electrode arrangement so that the electrode arrangement cleans the air from the pollutants while the polluted air passes through the electrode arrangement.

It should further be mentioned that the apparatus according to the invention can be portable or even hand-held.

Further, the apparatus according to the invention preferably comprises an integrated battery or electrically powering the electrode arrangement.

Moreover, the novel electrode arrangement can also be used for the treatment of mycosis, e.g. *tinea pedis*. The inventors have realized that the application of a non-thermal plasma to the skin surface of a patient quickly kills any mycosis even if the plasma is applied through socks. Therefore, the invention also encompasses a novel apparatus for the treatment of mycosis wherein the apparatus comprises an inlet opening through which the patients can introduce their feet. Then, the plasma is applied to the foot within the housing of the apparatus.

Another possible application for plasma treatment is the field of cosmetics. For example, a non-thermal plasma can be used for bleaching teeth.

Finally, the invention is also directed to a dressing, particularly a wound dressing, comprising a flexible and flat electrode arrangement as mentioned above for covering a body surface (e.g. a wound) of a patient. The integration of a DBD electrode arrangement into a wound dressing allows a plasma treatment of the wound while the wound is covered by the dressing.

The invention and its particular features and advantages will become apparent from the following detailed description considered with reference to the accompanying drawings.

DETAILED DESCRIPTION OF THE DRAWINGS

Figure 1A:
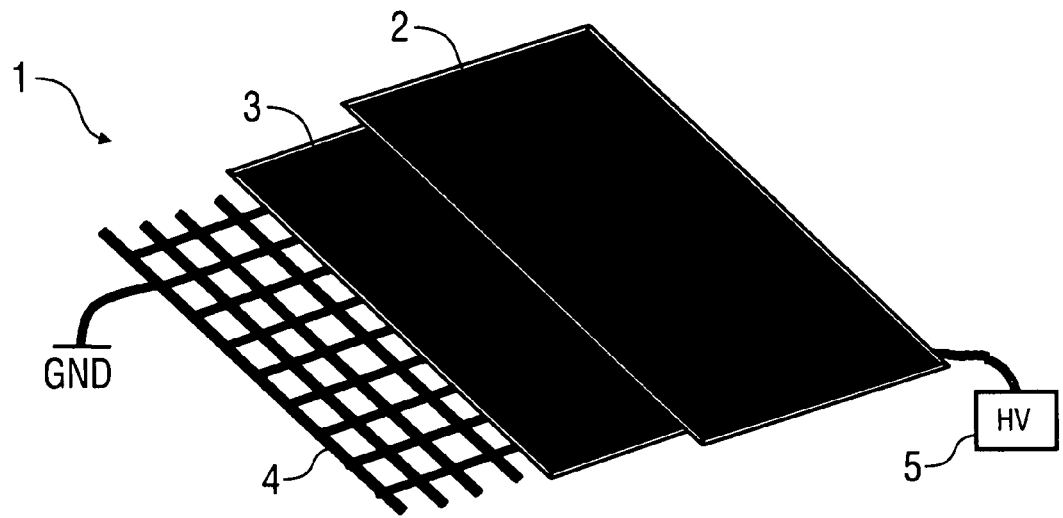
FIG. 1A shows a perspective view of a preferred embodiment of a DBD electrode arrangement according to the invention comprising a plate as a first electrode and a wire-mesh as a second electrode.
Figure 1B:
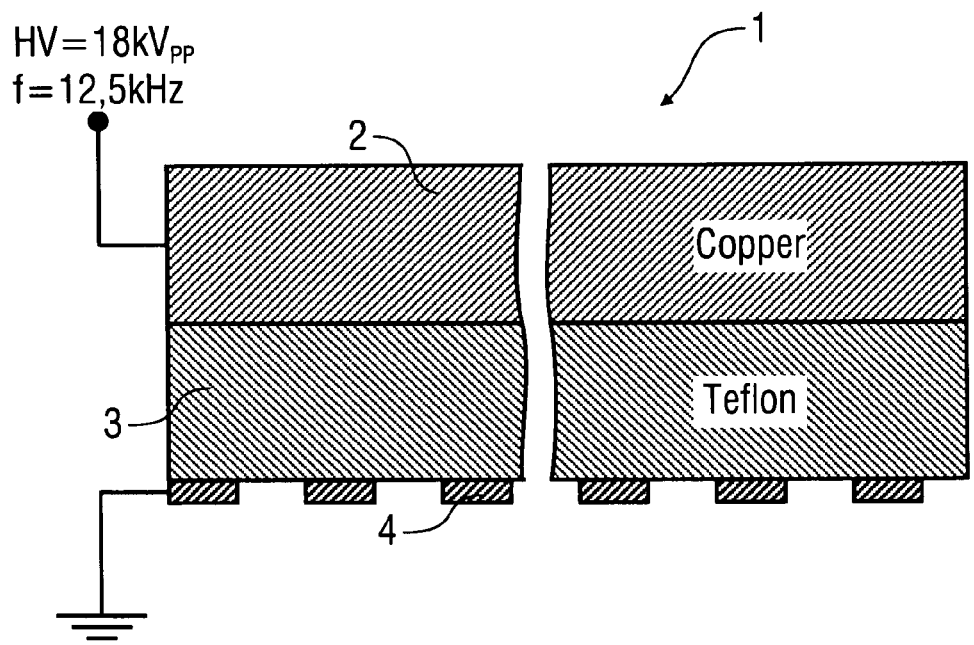
FIG. 1B shows a sectional view of the electrode arrangement according to FIG. 1A.

FIGS. 1A and 1B show a preferred embodiment of a DBD (dielectric barrier discharge) electrode arrangement 1 for generating a non-thermal plasma. The electrode arrangement 1 comprises a plate-shaped electrode 2 made of an electrically conductive material, e.g. copper or aluminium. The plate-shaped electrode 2 has a thickness in the range of 0.5-1 mm.

Further, the electrode arrangement 1 comprises a dielectric barrier 3 made of polytetrafluoroethylene, wherein the material of the dielectric barrier 3 is applied to the lower surface of the plate-shaped electrode 2.

Moreover, the electrode arrangement 1 comprises a further electrode 4 formed by a wire-mesh which is adhered to the dielectric barrier 3 on the side opposite the electrode 2.

The electrode 4 is electrically grounded while the other electrode 2 is electrically connected to a high voltage generator 5 which is applying an alternating current signal to the electrode 2 with a frequency of f=12.5 kHz and a peak-to-peak-voltage of HV=18 kV$_{pp}$. Therefore, the high voltage generator 5 triggers a dielectric discharge wherein the plasma is generated in the meshes of the mesh-shaped electrode 4.

Figure 2:
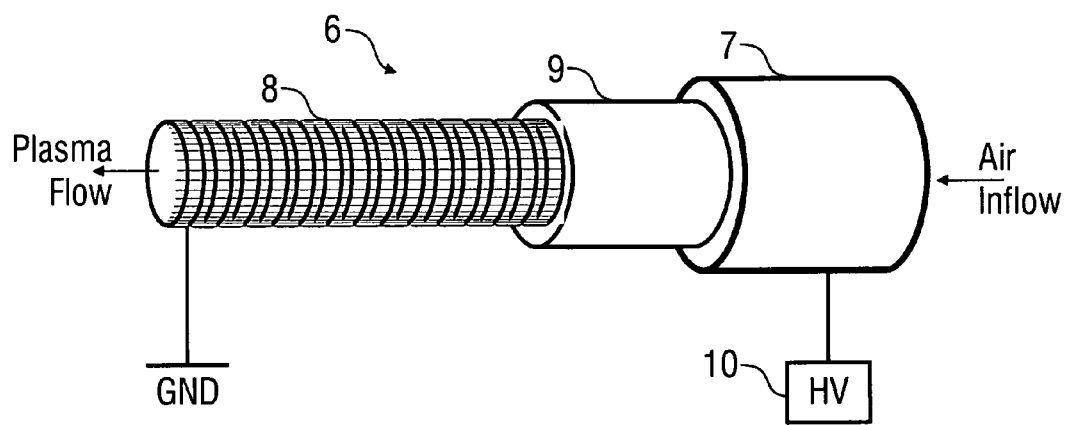
FIG. 2 shows a perspective view of a tube-shaped electrode arrangement.

FIG. 2 shows a tube-shaped electrode arrangement 6 for generating a non-thermal plasma wherein the representation is partially cut-away to illustrate the configuration of the electrode arrangement 6.

The tube-shaped electrode arrangement 6 comprises a massive outer electrode 7 made of an electrically conductive material wherein the outer electrode 7 is hollow and tube-shaped.

Further, the electrode arrangement 6 comprises an inner electrode 8 formed by a mesh made of an electrically conductive material.

The outer electrode 7 and the inner electrode 8 are separated by a tube-shaped dielectric barrier 9.

The outer electrode 7 is electrically connected to a high-voltage generator 10 as mentioned above while the inner electrode 8 is electrically grounded. Therefore, the high-voltage generator 10 triggers a dielectric barrier discharge wherein the non-thermal plasma is generated in the individual meshes of the inner electrode 8.

Figure 3:
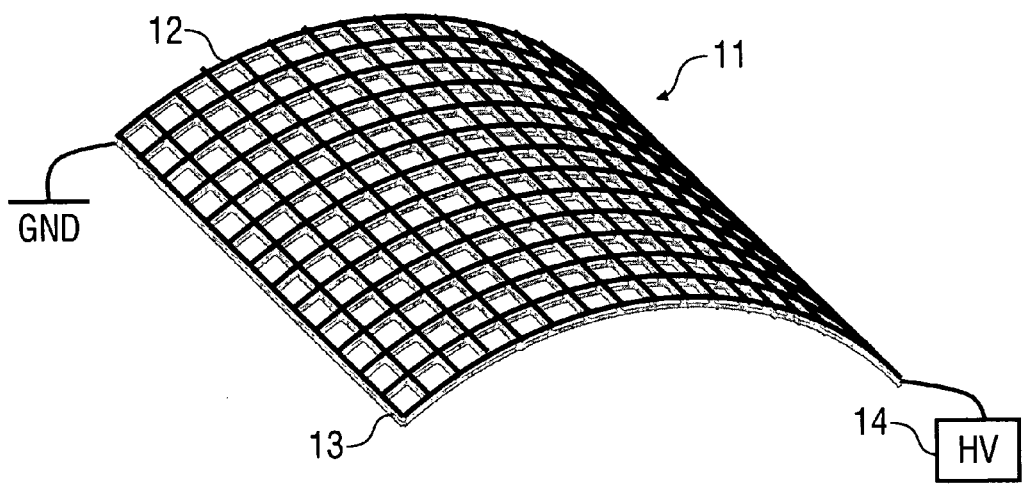
FIG. 3 shows a perspective view of an electrode arrangement comprising two wire-meshs.

FIG. 3 shows another embodiment of a two-dimensional electrode arrangement 11 similar to the electrode arrangement 1 shown in FIGS. 1A and 1B.

However, the electrode arrangement 11 comprises two mesh-shaped electrodes 12, 13, wherein the individual wires of at least one of the electrodes 12, 13 are surrounded by a cladding made of an electrically insulating and dielectric material forming a dielectric barrier between the electrodes 11, 12.

The electrode 13 is electrically grounded while the other electrode 12 is connected to a high-voltage generator 14 triggering a dielectric barrier discharge in the electrode arrangement 11 wherein the plasma is generated in the meshes of the electrodes 12, 13.

It should further be noted that the electrode arrangement 11 is flexible so that the shape of the electrode arrangement 11 can be adapted to any desired shape.

Figure 4:
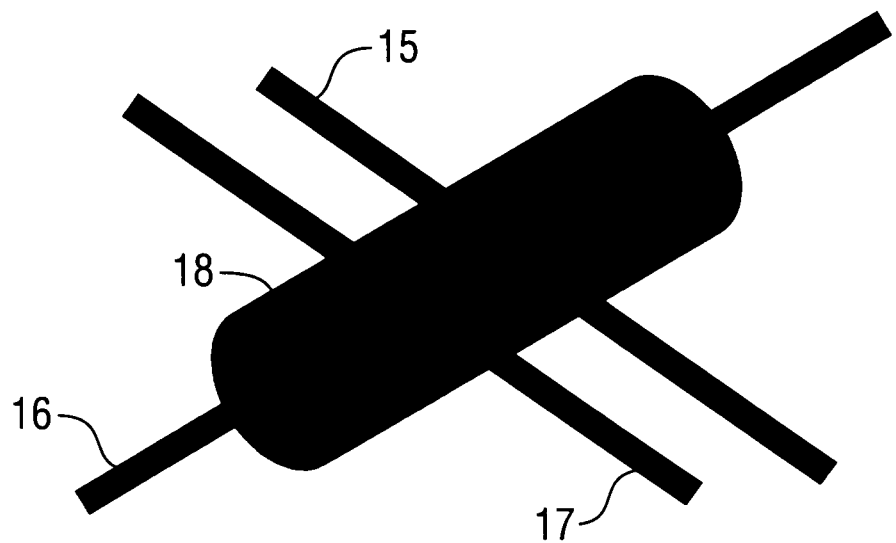
FIG. 4 shows a modification of the electrode arrangement according to FIG. 3 additionally comprising a cover.

FIG. 4 shows a junction between individual wires 15, 16, 17 of adjacent mesh-shaped electrodes. In this embodiment, the wire 16 is surrounded by a cladding 18 made of an electrically insulating and dielectric material thereby forming the dielectric barrier. The other wires 15, 17 are not insulated.

Figure 5:
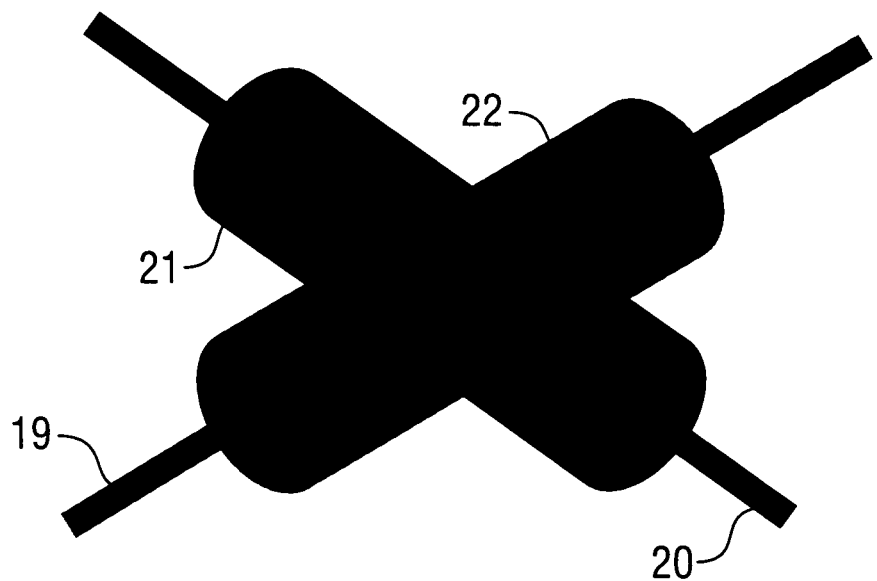
FIG. 5 shows a tube-shaped electrode arrangement comprising two linear electrodes within the tube.

FIG. 5 shows an other embodiment of a junction of wires 19, of adjacent mesh-shaped electrodes. In this embodiment both the wire 19 and the wire 20 is surrounded by a cladding 21, 22 made of an electrically insulating and dielectric material.

Figure 6:
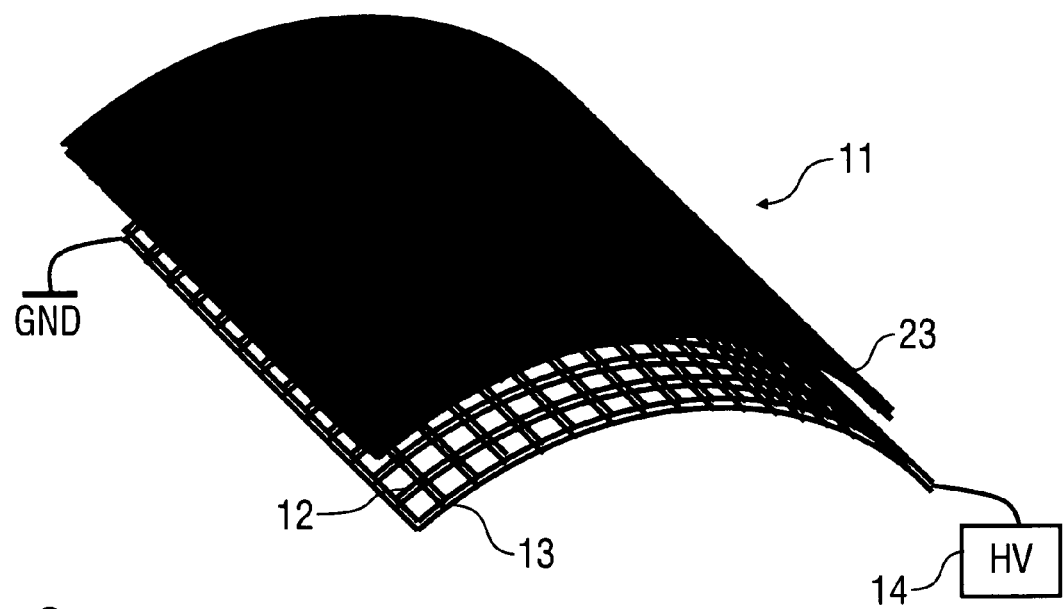
FIG. 6 shows a perspective view of a junction of the wires of several wire-meshs.

FIG. 6 shows a modification of the electrode arrangement shown in FIG. 3 so that reference is made to the above description relating to FIG. 3.

One characteristic feature of this embodiment is that the electrode arrangement 11 additionally comprises a cover 23. The cover can have different purposes, e.g. increasing the local density of reactive species, reducing the time for sterilization, filtering out unused reactive species, effecting a better control over the plasma or operating under reduced pressure.

Figure 7:
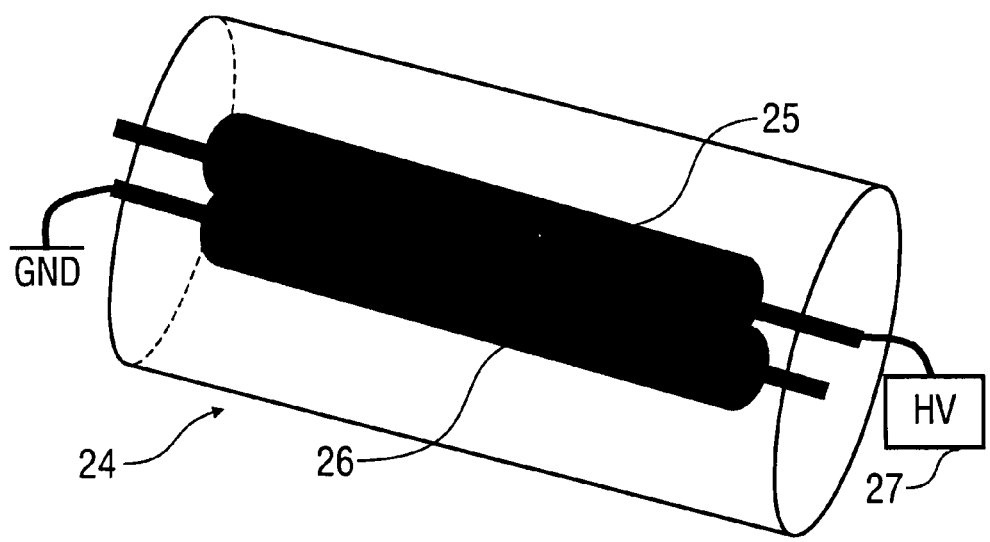
FIG. 7 shows a perspective view of a junction of two insulated wires.

FIG. 7 shows another embodiment of a tube-shaped electrode arrangement 24 comprising two linear electrodes 25, 26 each consisting of a wire surrounded by a cladding made of an electrically insulating and dielectric material forming a dielectric barrier.

The electrode 26 is electrically grounded while the other electrode 25 is electrically connected to a high-voltage generator 27 triggering a dielectric barrier discharge in the electrode arrangement 24.

Figure 8:
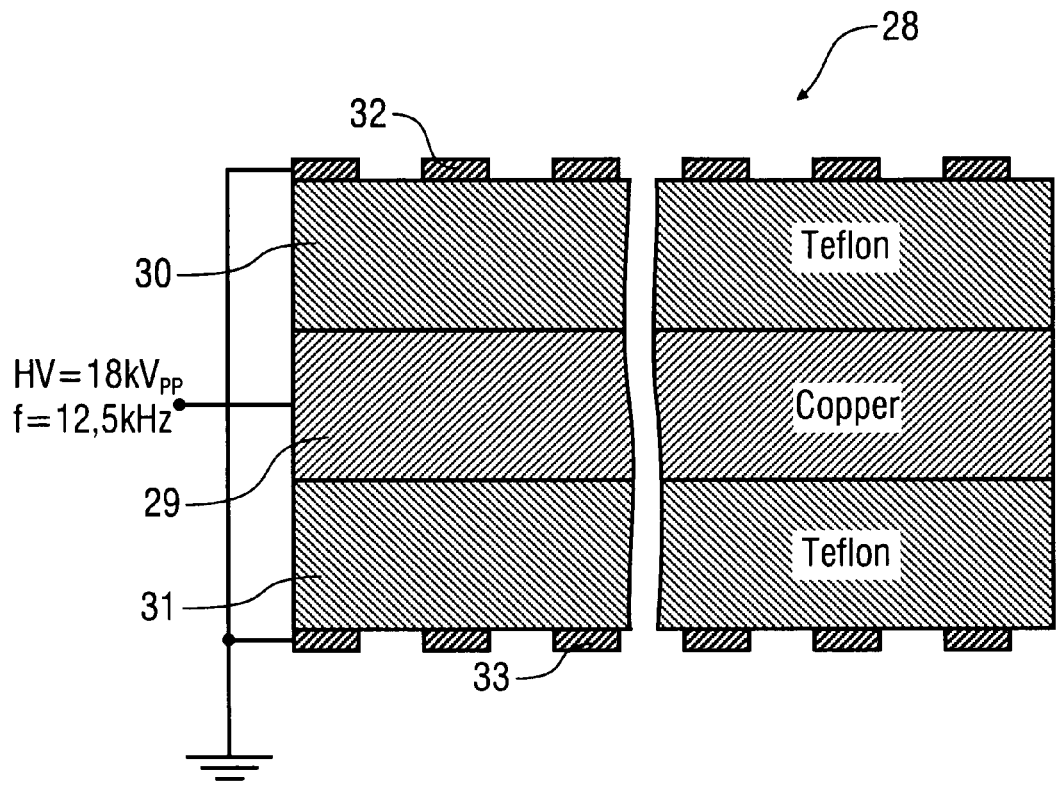
FIG. 8 shows a cross-sectional view of a sandwich-like DBD electrode arrangement comprising three electrodes.

FIG. 8 shows another embodiment of an electrode arrangement 28 suitable for generating a non-thermal plasma. The electrode arrangement 28 comprises a centre electrode 29 formed by a massive plate made of copper.

Further, the electrode arrangement 28 comprises two flat dielectric barriers 30, 31 each consisting of a flat plate made of polytetrafluoroethylene, wherein the dielectric barriers 30, 31 are attached to opposing sides of the centre electrode 29.

Further, the electrode arrangement 28 comprises two mesh-shaped outer electrodes 32, 33 which are attached to the outer sides of the dielectric barriers 30, 31.

The outer electrodes 32, 33 are electrically grounded while the centre electrode 29 is electrically connected to a high-voltage generator.

Figure 9:
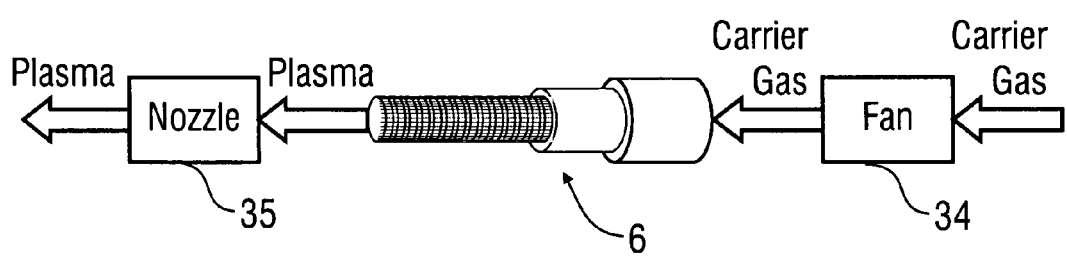
FIG. 9 shows a schematic view of the so-called plasma jet apparatus for generating a plasma jet.

FIG. 9 shows a so-called plasma jet apparatus for generating a plasma jet.

The plasma jet apparatus comprises the electrode arrangement 6 as shown in FIG. 2 for generating a non-thermal plasma.

Further, the plasma jet apparatus comprises a fan 34 for blowing a carrier gas into the tube-shaped electrode arrangement 6.

Finally, the plasma jet apparatus comprises a nozzle 35 which is attached to the outlet of the tube-shaped electrode arrangement 6 wherein the nozzle 35 is shaping the plasma jet leaving the electrode arrangement 6.

Figure 10:
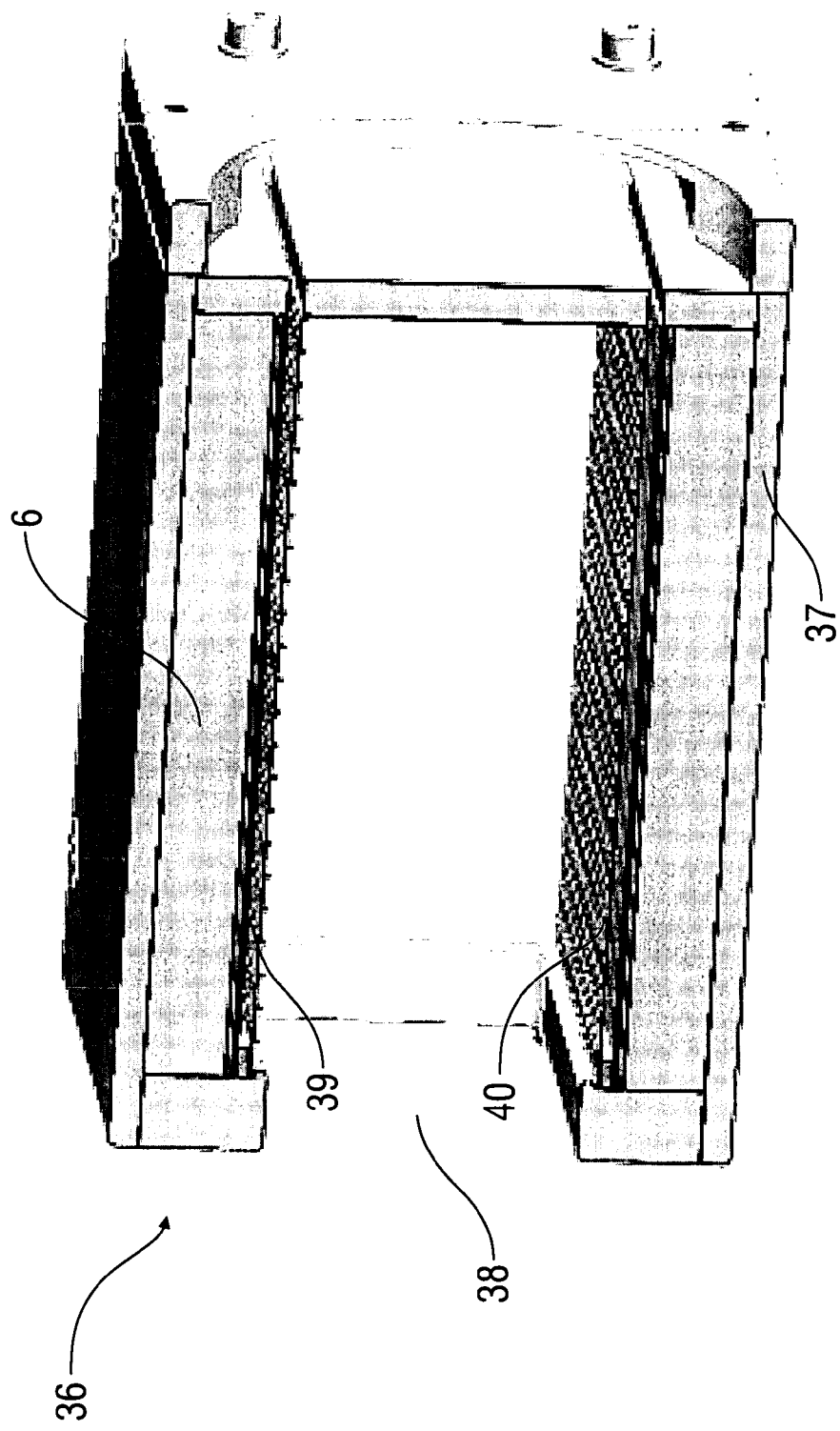
FIG. 10 shows a perspective sectional view of an apparatus for sterilizing hands.

Finally, FIG. 10 shows an apparatus 36 for sterilizing a hand by applying a non-thermal plasma to the hand. The apparatus 36 comprises a housing 37 for temporarily receiving the hand during the sterilization and an inlet opening 38 for introducing the hand into the housing 37.

Within the housing, there are two flat electrode arrangements 39, 40 above and below the area of treatment.

The apparatus 36 is described in more detail in EP 09 00 22 00.5 which is incorporated by reference herein.

Figure 11:
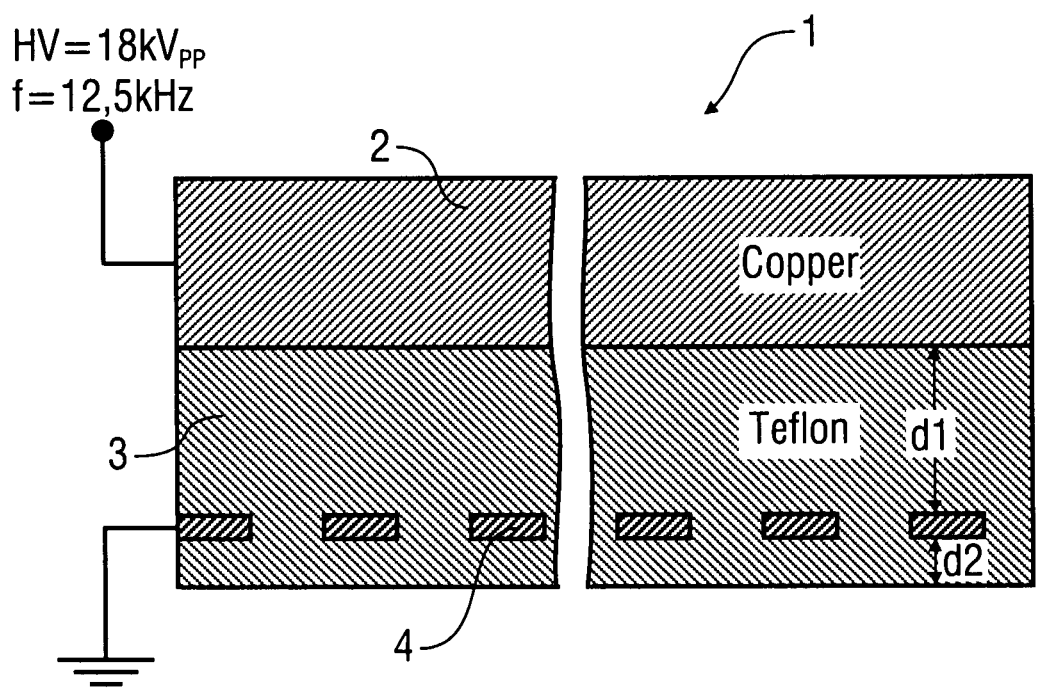
FIG. 11 shows a sectional view of a modification of the embodiment according to FIGS. 1A and 1B, wherein a wire-mesh is embedded into the dielectric barrier.

FIG. 11 shows a modification of the electrode arrangement shown in FIGS. 1A and 1B so that reference is made to the above description relating to FIGS. 1A and 1B. Further, the same reference numerals are used for corresponding parts and details.

One characteristic feature of the electrode arrangement 1 according to FIG. 11 is that the electrode 4 is embedded into the dielectric barrier 3. There is a distance d1=1 mm between the wire-mesh of the electrode 4 and the lower surface of the electrode 2. Further, there is a distance d2=0.1 mm between the wire-mesh of the electrode 4 and the outer surface of the dielectric barrier 3. It is essential that the distance d1 is greater than the distance d2. However, if it is desired to have a discharge on one side only, the embedded electrode 4 must be embedded more deeply than the distance d1 between the electrodes 2, 4.

If a flexible electrode arrangement 1 is desired, both electrodes 2, 4 are made of a flexible wire-mesh or parallel wires having a distance of approximately 1 cm, wherein the dielectric barrier 3 can be made of a flexible material, e.g. silicone rubber.

Although the invention has been described with reference to the particular arrangement of parts, features and the like, these are not intended to exhaust all possible arrangements of features, and indeed many other modifications and variations will be ascertainable to those of skill in the art.

LIST OF REFERENCE NUMERALS

1 Electrode arrangement
2 Electrode
3 Dielectric barrier
4 Electrode
5 High-voltage generator
6 Electrode arrangement
7 Outer electrode
8 Inner electrode
9 Dielectric barrier
10 High-voltage generator
11 Electrode arrangement
12 Electrode
13 Electrode
14 High-voltage generator
15 Wire
16 Wire
17 Wire
18 Cladding
19 Wire
20 Wire
21 Cladding
22 Cladding
23 Cover
24 Electrode arrangement
25 Electrode
26 Electrode
27 High-voltage generator
28 Electrode arrangement
29 Centre electrode
30 Dielectric barrier
31 Dielectric barrier
32 Outer electrode
33 Outer electrode
34 Fan
35 Nozzle
36 Apparatus
37 Housing
38 Inlet opening
39 Electrode arrangement
40 Electrode arrangement

The invention claimed is:

1. An apparatus for plasma treatment comprising an electrode arrangement for generating a non-thermal plasma comprising:
   a layer-shaped first electrode made of an electrically conductive material;
   a layer-shaped second electrode made of an electrically conductive material, wherein the second electrode is electrically insulated from the first electrode;
   a dielectric barrier arranged between the first electrode and the second electrode, so that the non-thermal plasma is generated by a dielectric barrier discharge, wherein at least one of the first electrode or the second electrode comprises a plurality of perforations which are distributed over the electrode,
      further wherein the electrode arrangement is shaped in the form of a hollow tube having an axially aligned inlet for introducing a carrier gas into the tube and an axially aligned outlet for dispensing the non-thermal plasma out of the tube so that the plasma is generated within the tube;
   a fan for blowing a carrier gas into the inlet of the electrode arrangement and axially through the electrode arrangement; and either or both of
   a nozzle attached to the outlet of the electrode arrangement for forming a plasma jet leaving the apparatus, and a guide pipe attached to the outlet of the electrode arrangement for directing the plasma jet in a specific direction, wherein the guide pipe comprises a flexible guide pipe so that the specific direction of the plasma jet is changeable by aiming the flexible guide pipe at a desired location of treatment.

2. The apparatus according to claim 1, wherein both the first electrode and second electrode comprise a wire-mesh, wherein the dielectric barrier comprises a cladding made of an electrically insulating and dielectric material surrounding the wires of at least one of the first electrode and the second electrode thereby electrically insulating the first electrode from the second electrode, and wherein the first electrode and the second electrode are attached to each other by an adhesive bond.

3. The apparatus according to claim 2, wherein both the first electrode and the second electrode are surrounded by an electrically insulating and dielectric cladding which forms the dielectric barrier.

4. The apparatus according to claim 2, wherein either the first electrode or the second electrode is surrounded by an electrically insulating and dielectric cladding which forms the dielectric barrier, and wherein the other of the first electrode or the second electrode is not insulated by a cladding.

5. The apparatus according to claim 1, wherein the apparatus is adapted to clean air of pollutants, comprising bacteria, viruses, or spores.

6. The apparatus according to claim 5, wherein
air axially passes through the electrode arrangement so that the electrode arrangement cleans the air of the pollutants while the air passes through the electrode arrangement.

7. The apparatus according to claim 1, wherein the first electrode and the second electrode are arranged within the tube.

8. The apparatus according to claim 7, wherein the first electrode and the second electrode are linear electrodes aligned substantially coaxially within the tube.

9. The apparatus according to claim 1, wherein
the apparatus is handheld or portable, and
the apparatus comprises an integrated battery for powering the electrode arrangement.

10. The apparatus according to claim 1, wherein at least one of the first electrode and the second electrode comprises a wire-mesh, wherein the plurality of perforations are arranged between members of the wire-mesh.

11. The apparatus according to claim 1, wherein at least one of the first electrode and the second electrode comprises a perforated plate in which the plurality of perforations are arranged.

12. The apparatus according to claim 1, wherein the first electrode comprises a plate made of an electrically conductive material, wherein the dielectric barrier is substantially layer-shaped and formed on a surface of the plate, and wherein the second electrode is formed on a surface of the dielectric barrier opposite the first electrode, wherein the second electrode comprises either a wire-mesh or a perforated plate.

13. The apparatus according to claim 1, further comprising a third electrode and a further dielectric barrier, such that there are two dielectric barrier discharge arrangements on both sides of a center electrode.

14. The apparatus according to claim 1, wherein the first electrode and the second electrode are adhered to each other and at least one of the first electrode and second electrode is embedded into the dielectric barrier.

15. The apparatus according to claim 1, wherein the dielectric barrier is adhered to either first electrode or the second electrode and at least one of the first electrode and second electrode is embedded into the dielectric barrier.

16. The apparatus according to claim 1, wherein at least one of the first electrode and the second electrode is surrounded by a cladding made of an electrically insulating and dielectric material forming the dielectric barrier.

17. The apparatus according to claim 1, further comprising a cover which covers the electrode arrangement, wherein the cover is adapted to accomplish any one or any combination of: increase the local density of the reactive species and reduce the time needed for sterilization, filter out unused reactive species, effect a better control over the plasma, and/or operate under reduced pressure.

18. The apparatus according to claim 1, wherein the dielectric barrier consists of a material selected from a group consisting of polytetrafluoroethylene and ceramics.

19. A wound dressing, comprising an electrode arrangement for covering a body surface of a patient, comprising:
a layer-shaped first electrode made of an electrically conductive material;
a layer-shaped second electrode made of an electrically conductive material, wherein the second electrode is electrically insulated from the first electrode; and
a dielectric barrier arranged between the first electrode and the second electrode, so that a non-thermal plasma is generated by a dielectric barrier discharge,
wherein at least one of the first electrode or the second electrode comprises a plurality of perforations which are distributed over the electrode, and wherein the electrode arrangement is substantially planar and deformable so that the shape of the electrode arrangement is adaptable to the contour of a body part which is to be treated, wherein both the first electrode and second electrode comprise a wire-mesh, wherein the dielectric barrier comprises a cladding made of an electrically insulating and dielectric material surrounding wires of at least one of the first electrode and the second electrode thereby electrically insulating the first electrode from the second electrode, and wherein the first electrode and the second electrode are attached to each other by an adhesive bond.

20. The wound dressing according to claim 19, wherein the electrode arrangement is flexible so that the shape of the electrode arrangement is adaptable to the body surface of the patient.

21. The wound dressing according to claim 19, wherein at least one of the first electrode and the second electrode comprises a wire-mesh, wherein the plurality of perforations are arranged between members of the wire-mesh.

22. The wound dressing according to claim 19, wherein at least one of the first electrode and the second electrode comprises a perforated plate in which the plurality of perforations are arranged.

23. The wound dressing according to claim 19, wherein the first electrode comprises a plate made of an electrically conductive material, wherein the dielectric barrier is substantially layer-shaped and formed on a surface of the plate, and wherein the second electrode is formed on a surface of the dielectric barrier opposite the first electrode, wherein the second electrode comprises either a wire-mesh or a perforated plate.

24. The wound dressing according to claim 19, wherein both the first electrode and the second electrode are surrounded by an electrically insulating and dielectric cladding which forms the dielectric barrier.

25. The wound dressing according to claim 19, wherein either the first electrode or the second electrode is surrounded by an electrically insulating and dielectric cladding which forms the dielectric barrier, and wherein the other of the first electrode or the second electrode is not insulated by a cladding.

26. The wound dressing according to claim 19, further comprising a third electrode and a further dielectric barrier, such that there are two dielectric barrier discharge arrangements on both sides of a center electrode.

27. The wound dressing according to claim 19, wherein the first electrode and the second electrode are adhered to each other and at least one of the first electrode and second electrode is embedded into the dielectric barrier.

28. The wound dressing according to claim 19, wherein the dielectric barrier is adhered to either first electrode or the second electrode and at least one of the first electrode and second electrode is embedded into the dielectric barrier.

29. The wound dressing according to claim 19, wherein the electrode arrangement is configured to be any one or any combination of substantially flat, substantially planar, and substantially curved.

30. The wound dressing according to claim 19, further comprising a cover which covers the electrode arrangement, wherein the cover is adapted to accomplish any one or any combination of: increase the local density of the reactive species and reduce the time needed for sterilization, filter out unused reactive species, effect a better control over the plasma, and/or operate under reduced pressure.

31. The wound dressing according to claim 19, wherein the dielectric barrier consists of a material selected from a group consisting of polytetrafluoroethylene and ceramics.

* * * * *